US008652094B2

(12) United States Patent
David et al.

(10) Patent No.: US 8,652,094 B2
(45) Date of Patent: Feb. 18, 2014

(54) SYRINGE WITH UNIVERSAL END-PIECE

(75) Inventors: Olivier David, Les Portes (FR); Emeric Mermet, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 12/993,728

(22) PCT Filed: May 27, 2009

(86) PCT No.: PCT/IB2009/006075
§ 371 (c)(1),
(2), (4) Date: Feb. 10, 2011

(87) PCT Pub. No.: WO2009/144583
PCT Pub. Date: Dec. 3, 2009

(65) Prior Publication Data
US 2011/0130717 A1    Jun. 2, 2011

(30) Foreign Application Priority Data

May 30, 2008  (FR) ...................................... 08 02978

(51) Int. Cl.
*A61M 5/30* (2006.01)
(52) U.S. Cl.
USPC ............................................. 604/68; 604/72
(58) Field of Classification Search
USPC ........... 604/68, 72, 70, 71, 86, 88, 89, 90, 91, 604/232, 500, 533; 33/494; 29/890.126
See application file for complete search history.

(56) References Cited

U.S. PATENT DOCUMENTS

| 4,596,561 | A | | 6/1986 | Meyer et al. |
| 5,312,335 | A | * | 5/1994 | McKinnon et al. ............. 604/72 |
| 5,694,686 | A | * | 12/1997 | Lopez ..................... 29/890.126 |
| 5,964,737 | A | | 10/1999 | Caizza |
| 7,931,614 | B2 | * | 4/2011 | Gonnelli et al. ................ 604/68 |
| 2008/0033347 | A1 | | 2/2008 | D'Arrigo et al. |

FOREIGN PATENT DOCUMENTS

| WO | 8805668 A1 | 8/1988 |
| WO | 2004069037 A2 | 8/2004 |

* cited by examiner

*Primary Examiner* — Nicholas Lucchesi
*Assistant Examiner* — Brooke Matney
(74) *Attorney, Agent, or Firm* — Hoffmann & Baron, LLP

(57) ABSTRACT

The present invention relates to a syringe (20) defining a reservoir (21) for containing a liquid and comprising an end-piece (10) encompassing a channel (11) providing a passageway for the transfer of the said liquid, characterized in that the said channel (11) comprises two portions, a first portion (12) and a second portion (13), the said first portion (12) extending from the free distal end (14) of the end-piece (10) in the direction of the reservoir (21), and the said second portion (12) extending between the first portion (12) of the channel (11) and the proximal end (15) of the end-piece (10) and connecting the said first portion (12) to the reservoir, the said first portion (12) having an average diameter that is greater than the average diameter of the said second portion (13).

21 Claims, 2 Drawing Sheets

SYRINGE WITH UNIVERSAL END-PIECE

Figure 1A:
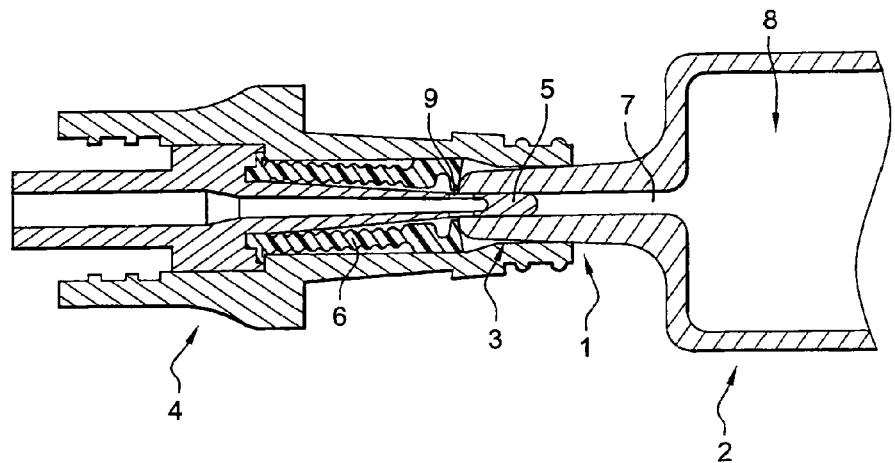

The present invention relates to a conventional or pre-filled syringe having an end-piece suitable for the mounting of needleless connectors, which are connected for example via a conical assembly, for example by a 6% conical assembly of the "Luer" type.

In this application, the distal end of a component or of a device must be understood as meaning the end furthest from the hand of the user and the proximal end must be understood as meaning the end closest to the hand of the user.

Various medical devices are known for transferring and/or storing medical fluids, such as syringes, perfusion and transfusion devices and connectors. It is essential that these various medical devices can be assembled together correctly and securely.

Conical assemblies, for example the 6% conical assemblies of the Luer type, whose specifications are defined by precise standards (see in particular the ISO 594/1 86 and ISO 594/2 98 standards), make it possible to ensure compatibility for the mounting of the various types of medical devices. These specifications apply to the conical assemblies made of rigid or semi-rigid materials.

A conventional syringe usually comprises a hollow body forming a reservoir for a medical liquid to be ejected from or tapped into the said syringe, a seal placed inside the body to delimit the said reservoir at one of its ends, in particular at its proximal end, and a rod for actuating the seal forming a piston with a proximal holding portion. In addition, the distal end of the body forming the reservoir usually comprises an end-piece in which an axial passageway is arranged through which the said liquid is ejected from the reservoir. The end-piece may comprise an external distal junction bearing surface for friction sleeve-fitting, for example of the "Luer" type of frustoconical shape.

The handling of liquids, in particular for a parenteral administration to a patient which is carried out via a perfusion device, as often in hospitals or in emergency situations, implies, in a general manner, the use of connectors and couplings furnished with conical assemblies, for example 6% Luer conical assemblies. A connector that is frequently used, and hereinafter called the Clave® type, is described, for example, in U.S. Pat. No. 5,694,686. This connector comprises in particular an internal sheathed canula, attached to the inside of a female Luer conical assembly, designed to enter the axial passageway of the end-piece of a syringe. Such connectors make it possible to seal assemblies of medical devices and provide protection against the contamination of the medical liquids that they contain. However, problems have been reported concerning the use of this type of connector with various syringes that turned out to be incompatible. The use of adapted intermediate couplings is then often required, which complicates the intervention of the medical staff, particularly in emergency situations. In addition, the attempt to install a syringe that is incompatible with such a connector may make the syringe and/or the connector unusable because of a breakage of the end-piece of the syringe and/or of the internal canula of the connector. In such a case, the administration of the medicine is made impossible or, at best, delayed.

The sheathed internal canula present within the connector as described in U.S. Pat. No. 5,694,686 requires a minimum diameter of the axial passageway of the end-piece of the syringe in order to ensure a correct mounting of the said connector in and of the syringe and to allow medical fluids to travel between the connector and the syringe. Additionally, the external diameter of the free end of the end-piece of the syringe and its conicity are imposed by standards (see standards ISO 594/1 86 and ISO 594/2 98) if it is desired to provide compatibility with other devices with conical assemblies, for example 6% Luer. Finally, the diameter of the axial passageway is also limited by the need for the end-piece to have a thickness of the walls forming it that is sufficient to ensure that the said walls offer an appropriate resistance in order to withstand, on the one hand, the operations of manufacture of the said end-piece and, on the other hand, the insertion of the said end-piece into a conical assembly such as for example a 6% Luer female conical assembly, without breaking the said walls. This problem of breakage of the walls of the end-piece is all the more important when the material used to manufacture the syringe and the end-piece is chosen from breakable materials such as glass.

Furthermore, if a medical liquid is transferred from the syringe to another device by means of a connector, it is desirable for the volume of medical liquid remaining in the end-piece after the transfer of the medical liquid, which constitutes what is called the "dead volume", to be as small as possible in order, on the one hand, to minimize the wastage of medical liquid and, on the other hand, for reasons of accuracy of the volume of medical liquid administered.

The subject of the present invention is a syringe having an end-piece making it possible to solve the compatibility problems encountered with the connectors comprising an internal canula. Preferably, the syringe according to the invention also makes it possible to solve the problems of compatibility with conical assembly connectors. The syringe of the present invention also makes it possible, during its connection for example to a perfusion device, to avoid the use of additional couplings that are not always immediately available, in particular in emergency situations, which add an additional handling step and which increase the dead volume of the medical installation.

The syringe of the present invention has an end-piece making it possible to reduce the dead volume of the axial passageway of the end-piece.

One aspect of the present invention is a syringe defining a reservoir for containing a liquid and comprising an end-piece having a longitudinal axis A, the said end-piece encompassing a channel aligned with the said longitudinal axis A and providing a passageway for the transfer of the said liquid, characterized in that the said channel comprises at least two portions, a first portion and a second portion, the said first portion extending from a free distal end of the end-piece in the direction of the reservoir, and the said second portion extending between the first portion of the channel and a proximal end of the end-piece and connecting the said first portion to the reservoir, the said first portion having an average diameter that is greater than the average diameter of the said second portion, each of said first and second portions having the shape of a cylinder.

In the present application, "average diameter" means the diameter resulting from the average of the various diameters measured by taking several cross sections over a certain length of a part.

In the present application, "diameter" means a diameter corresponding to a determined cross section of a part.

Therefore, in the present application, the first portion and the second portion each have a certain length. For each portion, the diameter is capable of slightly varying over the length of the said portion, for example according to the material used, or to the manufacturing method used. For each portion, the average diameter corresponds to the average of the various diameters that can be measured over the length of the said portion. Each portion has the shape of a cylinder: in other words, for each portion, the average diameter is substantially constant. Such cylindrical portions allow a better flow of the medical liquid when expelled through the passageway, an easy manufacturing, a suitable connection with connectors comprising an internal canula that have the shape of a cylinder and a reduction of the dead volume. The first portion of the channel of the end-piece of the syringe according to the invention makes it possible to allow compatibility of the assembly of the said syringe with a connector while the second portion of the channel of the end-piece of the syringe confers on the end-piece sufficient strength to prevent breakage when the said end-piece is inserted into a conical assembly, for example in a female 6% Luer conical assembly.

In one embodiment of the invention, the said first portion is suitable for mounting a needleless connector system, in particular a needleless connector system of the Clave® type, as described in U.S. Pat. No. 5,694,686.

Also advantageously, a transition zone connects the said first portion and the said second portion together, the said transition zone having a length along the longitudinal axis A of the said end-piece greater than 0, the diameter of the said transition zone varying along the said length within a range defined by the average diameter of the said first portion and the average diameter of the said second portion.

In one embodiment of the invention, the transition zone has a partially spherical shape. In another embodiment of the invention, the transition zone has a frustoconical shape. Such partially spherical or frustoconical shapes have the advantages of optimizing the strength of the end-piece and making it possible to reduce the dead volume. Furthermore, such shapes also make it possible to facilitate the manufacturing method, in particular when the end-piece is made of a breakable material such as glass.

In one embodiment of the syringe according to the invention, the external shape of the end-piece is compatible with a connector of the Luer type. In particular, the external shape of the end-piece of the syringe according to the invention may be conical. For example, the external shape of the end-piece may have a 6% conicity in order to be compatible with a Luer-type connector having a 6% conicity. Such an external shape of the end-piece makes it possible to ensure the compatibility of the syringe according to the present invention with the other medical devices intended to be assembled via a conical assembly.

Therefore, preferably, the end-piece of the syringe according to the invention has a symmetry of revolution relative to its longitudinal axis A. The external diameter of the proximal end of the end-piece may then advantageously lie within the range from 4.30 to 4.50 mm. The external diameter of the distal end of the end-piece may advantageously lie within the range from 3.90 to 4.10 mm. The average diameter of the second portion of the channel may lie within the range from 1.00 to 1.30 mm. The average diameter of the first portion of the channel may lie within the range from 1.60 to 1.90 mm. The length of the first portion of the channel along the longitudinal axis A of the end-piece may lie within the range from 5.60 to 7.00 mm. The length of the transition zone may lie within the range from 0.30 to 2.00 mm. An end-piece of a syringe according to the invention having at least one of the dimensions, preferably all of the dimensions, mentioned in this paragraph is particularly useful and suitable for a safe, rapid, simple and effective assembly, with no risk of breakage or incompatibility, with a device comprising a Luer-type connector with conical assembly, such as for example a 6% conicity Luer connector, and/or a device comprising a needleless-type connector, such as for example a Clave® connector.

The conservation of certain medical liquids may impose constraints on the material used for the syringe. For example, for medical liquids requiring great stability, it is preferable to use glass. A material such as glass makes it possible to conserve in the syringe particular medical liquids, whose stability and/or integrity could be compromised if they were conserved in a plastic syringe. Glass is therefore particularly advantageous in the case of pre-filled syringes. Glass however has the disadvantage of being fragile and of breaking easily.

The syringe according to the invention, because of the particular structure of its end-piece, makes it possible to produce a secure and effective connection, with no risk of breakage of the said end-piece, with connectors of the Luer type or with needleless connectors of the Clave® type, even if the syringe and its end-piece are made in a single piece out of glass.

Therefore, in one embodiment of the invention, the syringe and the end-piece are made in a single piece out of glass. For example, the glass may be borosilicate glass.

Furthermore, a material such as glass also makes it possible to produce syringes that are stable to severe sterilization treatments, such as for example steam or ethylene oxide sterilization. The syringe end-piece according to the invention, in particular when the syringe and the end-piece are made of glass, may also comprise a circular groove suitable for assembling a Luer Lock adapter to the said end-piece, the said circular groove being situated on the outer surface of the end-piece, between the proximal end of the end-piece and the transition zone of the channel. Then advantageously the syringe may be furnished with a Luer Lock adapter.

For example, the said circular groove having a length along the longitudinal axis A of the end-piece defining a proximal edge and a distal edge of the said circular groove, the distal edge of the circular groove is situated at a distance of at least 7.50 mm from the free distal end of the end-piece. Therefore, for example, it is possible to furnish the syringe according to the invention with a Luer Lock adapter.

In another embodiment, the syringe and its end-piece are made of polymer, chosen for example from polycarbonate, polypropylene, the cyclo olefin copolymers (COC) and their blends. Such a polymer material makes for easier shaping.

The syringe according to the present invention may be pre-filled.

Figure 1B:
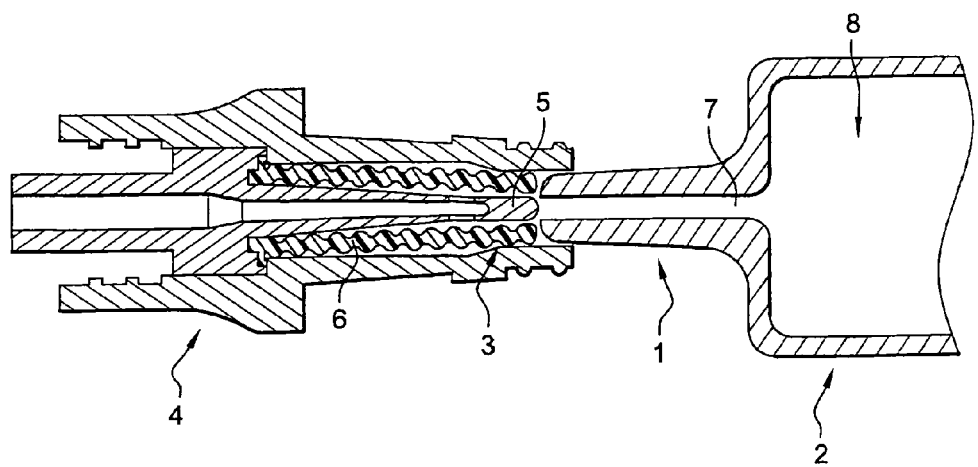

The invention and the advantages that arise therefrom will clearly emerge from the detailed description that is given below with reference to the appended drawings in which:

FIGS. 1a and 1b represent views in partial cross section of syringes of the prior art and their end-piece, that the user attempts to insert into a connector comprising an internal canula such as those described in U.S. Pat. No. 5,694,686.

Figure 2:
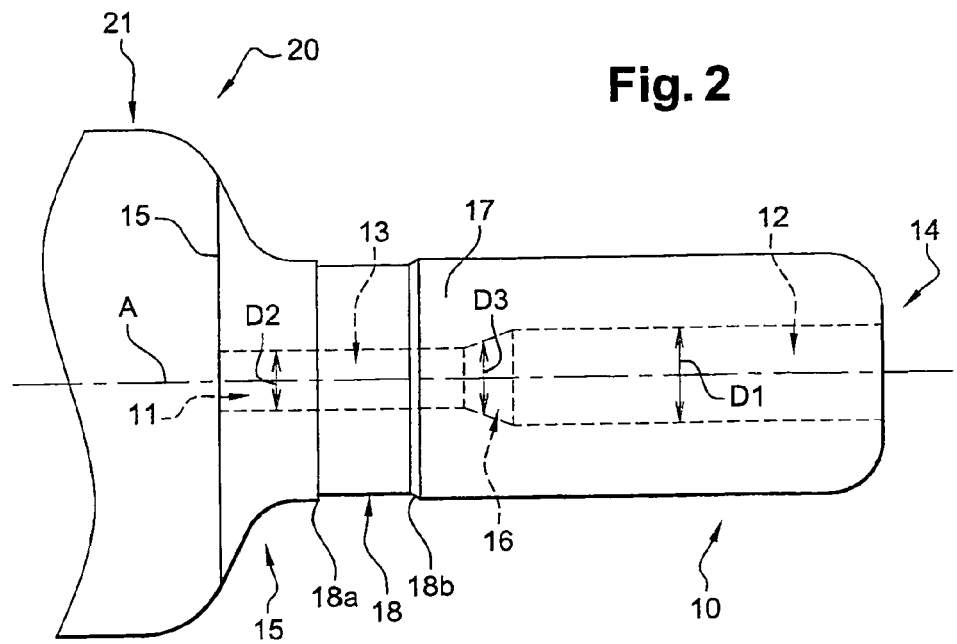
Figure 3:
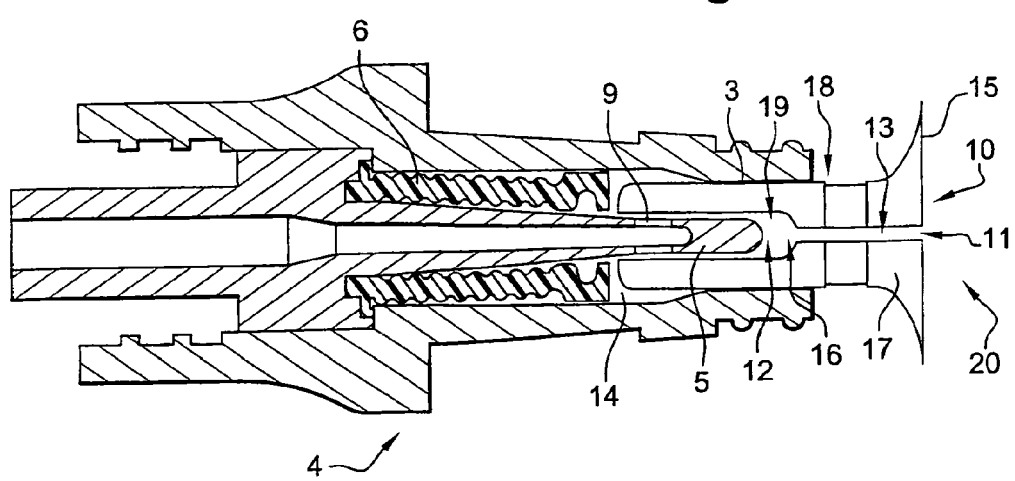

FIG. 2 represents a side view of the end-piece of a syringe according to the invention, FIG. 3 represents a view in section of the end-piece of the syringe of FIG. 2 mounted on a connector as shown in FIG. 1.

FIG. 1a represents the end-piece 1 of a syringe 2 of the prior art of which the user has attempted to insert the end-piece 1 into the female conical assembly 3 of a needleless connector 4, for example of the Clave® type, having an internal canula 5 sheathed by a retractable seal 6. The end-piece 1 of the syringe 2 of the prior art comprises an axial passageway in the form of a duct 7 having the same cross section, relative to the longitudinal axis of the end-piece 1, over the whole length of this duct 7. The conical shape of the internal canula 5 and the single diameter of the duct 7 of the end-piece 1 prevent the internal canula 5 from sufficiently entering the said duct 7 in order to allow the medical liquid, for example contained in the reservoir 8 of the syringe 2, to travel through the assembly via the apertures 9 arranged in the internal canula 5. The syringe 2 of the prior art and its end-piece 1 are therefore incompatible with the connector 4. An assembly consisting of the syringe 2 of the prior art and a connector 4 is therefore unusable and makes the administration of the medical liquid impossible.

FIG. 1*b* represents another syringe 2 of the prior art comprising a duct 7 having an end-piece 1 whose internal diameter does not make it possible to receive the canula 5 of the connector 4: this canula 5 does not enter the duct 7 at all: connection between the syringe 2 and the connector 4 is impossible.

FIG. 2 represents a syringe 20 according to the invention (partially shown in the figure) defining a reservoir 21 (partially shown) for containing a liquid, for example a medical liquid, comprising an end-piece 10 having a longitudinal axis A. The end-piece 10 encompasses a channel 11 aligned along the longitudinal axis A providing a passageway for the transfer of the liquid to be ejected from or tapped into the syringe 20 towards the distal end 14 of the end-piece 10. The channel 11, in the example shown, comprises two portions, a first portion 12 and a second portion 13. The said first portion 12 extends from the free distal end 14 of the end-piece 10 in the direction of the reservoir 21 of the syringe 20 according to the invention. This portion 12 is for example adapted for the mounting of a needleless connector system 4 such as that shown in FIG. 1 for example. The said second portion 13 extends between the first portion 12 of the channel 11 and the proximal end 15 of the end-piece 10 while connecting the said first portion 12 with the reservoir 21, the said first portion 12 having an average diameter D1 that is greater than the average diameter D2 of the said second portion 13. As appears from FIG. 2, each portion (12, 13) has the shape of a cylinder. In other words, for each portion, ie the first portion 12 and the second portion 13 respectively, the average diameter, D1 and D2 respectively, is substantially constant. In addition, in the example shown, the first and second portions (12, 13) are connected together via a transition zone 16 having a non-zero length along the longitudinal axis A of the end-piece 10. As appears in this figure, the diameter D3 of the transition zone 16 varies along its length within a range defined by the average diameter of the said first portion 12 and the average diameter of the said second portion 13. In the example shown in FIG. 2, the transition zone 16 has a frustoconical shape. In another embodiment, not shown, the transition zone 16 has a partially spherical shape. Such shapes, partially spherical or frustoconical, have the advantage of reinforcing the strength of the end-piece 10, in particular at its wall 17, more precisely when the latter is made of glass. Such shapes also make it possible to reduce the dead volume, corresponding in the example shown to the volume represented by the first and second portions (12,13) and the transition zone 16. Furthermore, such shapes also make it possible to facilitate the manufacturing method, in particular when the end-piece 10 is made of a breakable material such as glass.

The end-piece 10 shown in FIG. 2 preferably has a symmetry of revolution relative to its longitudinal axis A; in such a case, the end-piece 10 preferably has at least one of the following dimensions:

a) the external diameter of the proximal end of the end-piece 10 lies within the range from 4.30 to 4.50 mm, b) the external diameter of the free distal end 14 of the end-piece 10 lies within the range from 3.90 to 4.10 mm, c) the average diameter of the second portion 13 of the channel 11 lies within the range from 1.00 to 1.30 mm, d) the average diameter of the first portion 12 of the channel 11 lies within the range from 1.60 to 1.90 mm, e) the length of the first portion 12 of the channel 11 along the longitudinal axis A of the end-piece 10 lies within the range from 5.60 to 7.00 mm, f) the transition zone 16 has a length along the longitudinal axis lying within the range from 0.30 to 2.00 mm, g) the external shape of the end-piece has a 6% conicity.

An end-piece of a syringe according to the invention having at least one of the dimensions, preferably all of the dimensions, specified above is particularly useful and suitable for a safe, rapid, simple and effective assembly, with no risk of breakage or incompatibility, with a device comprising a conical assembly Luer-type connector, such as for example a 6% conicity Luer connector, and/or a device comprising a needleless-type connector, such as for example a Clave® connector.

For example, an end-piece of a syringe according to the invention having the features a) and c) in combination makes it possible to obtain an excellent strength of the walls of the end-piece, even if the latter are made of glass, and a reduction of dead volume.

For example, an end-piece of a syringe according to the invention having the features b), d), e) and g) is particularly compatible with all types of connectors, for example Luer connectors and Clave® connectors.

In one embodiment, the syringe and the end-piece are made in a single piece of glass, for example borosilicate glass.

The end-piece of the syringe according to the invention may comprise, as shown in FIG. 2, a circular groove 18 suitable for assembling a Luer Lock adapter to the said end-piece 10 (see FIG. 3), the said circular groove 18 being situated on the outer surface of the said end-piece 10 between the proximal end 15 of the end-piece 10 and the transition zone 16 of the channel 11.

The circular groove 18 is therefore offset, along the longitudinal axis A of the end-piece, relative to the transition zone 16 in order to prevent weakening the said wall 17. For example, the said circular groove 18 has a length along the longitudinal axis A of the end-piece 10 defining a proximal edge 18*a* and a distal edge 18*b* of the said circular groove, and the distal edge 18*b* of the circular groove 18 is then situated at a distance of at least 7.50 mm from the free end 14 of the end-piece 10. Such an end-piece 10 is particularly suitable for connection with a Luer type connector, even if this end-piece 10 is made of glass.

In another embodiment of the invention, the end-piece 10 may be made of polycarbonate.

The end-piece 10 of a syringe according to the invention is particularly advantageous for solving the problems encountered with syringes made of breakable materials such as glass, more particularly of borosilicate glass. Specifically, despite the problems of intrinsic fragility of glass syringes, the latter often allow a better conservation of the medical fluids and medicines that they contain. It is therefore desirable to prepare pre-filled glass syringes. In this case, the syringe according to the invention is particularly suitable for solving the problems posed by this type of syringe. Finally, glass syringes allow easier decontamination with the aid for example of sterilizing gas.

Preferably, the external shape of the end-piece 10 is compatible with connection with a Luer-type connector, for example the end-piece 10 of the syringe according to the invention complies in particular with the dimensions imposed by the standards defining Luer 6% conical assemblies.

FIG. 3 represents the syringe 20 (shown partially) and its end-piece 10 of FIG. 2, mounted on a connector 4 such as that shown in FIG. 1. The average diameter of the first portion 12 of the channel 11 being greater than that of the second portion 13, it allows the internal canula 5 of the connector 4 to correctly enter the channel 11 of the end-piece 10 and therefore allow the medical liquid to travel through the windows 9 of the internal canula 5 in the intermediate space 19 released between the wall 17 of the end-piece 10 and the internal canula 5, without risking breakage of the end-piece 10. Specifically, the second portion 13 having a narrower cross section, it makes it possible to increase the thickness of the walls 17 and therefore to globally reinforce the end-piece 10. In addition, such a narrower cross section of the second portion 13 makes it possible to reduce the dead volume of the assembly corresponding to the volume of the intermediate space 19 added to the volume of the second portion 13 and of the transition zone 16.

The free end 14 of the end-piece 10 presses on the retractable seal 6. In one embodiment of the invention, the surface of the said free end 14 of the end-piece 10 is preferably substantially smooth. Such a configuration makes it possible to ensure a correct seal of the assembly formed by the end-piece 10 and the connector 4.

Therefore, as shown in FIG. 3, the syringe according to the invention and its end-piece make it possible to produce in a safe, simple and effective manner assemblies of the said syringe with needleless connectors of the Clave® type and assemblies of this same syringe with connectors of the Luer type or Luer Lock type adapters, and to do so even if the syringe and its end-piece are made in a single piece of a breakable material such as glass.

The invention claimed is:

1. Syringe (20) defining a reservoir (21) for containing a liquid and comprising an end-piece (10) having a longitudinal axis A, the said end-piece (10) encompassing a channel (11) aligned with the said longitudinal axis A and providing a passageway for the transfer of the said liquid, characterized in that the said channel (11) comprises at least two portions, a first portion (12) and a second portion (13), the said first portion (12) extending from a free distal end (14) of the end-piece (10) in the direction of the reservoir (21), and the said second portion (13) extending between the first portion (12) of the channel (11) and a proximal end of the end-piece (10) and connecting the said first portion (12) to the reservoir (21), the said first portion (12) having an average diameter that is greater than the average diameter of the said second portion (13), each of said first and second portions having the shape of a cylinder, a proximalmost diameter of said first portion (12) being greater than a distalmost diameter of said second portion (13), a transition zone (16) being defined between, and connecting, said first and second portions (12, 13), said transition zone (16) including a distally-facing wall, having a length greater than 0, extending between said proximalmost diameter of said first portion (12) and said distalmost diameter of said second portion (13), said distally-facing wall protrudes radially-inwardly with a change in diameter from said proximalmost diameter of said first portion (12) to said distalmost diameter of said second portion (13) so as to define a step between said first portion (12) and said second portion (13), said change in diameter of said distally-facing wall over the length of said distally-facing wall being greater than a change in diameter over a length of said second portion equal to a length of said distally-facing wall adjacent to said distally-facing wall, wherein, said first portion, said transition zone and said second portion are open to define said passageway for the transfer of said liquid between the reservoir and the free distal end of the end-piece, wherein the syringe and the end-piece are made in a single piece out of glass.

2. Syringe (20) according to claim 1, characterized in that the said first portion (12) is suitable for mounting a needleless connector system (4).

3. Syringe (20) according to claim 1, characterized in that the diameter of the said transition zone (16) varying along the said length within a range defined by the average diameter of the said first portion (12) and the average diameter of the said second portion (13).

4. Syringe (20) according to claim 1, characterized in that the transition zone (16) has a partially spherical shape.

5. Syringe (20) according to claim 1, characterized in that the transition zone (16) has a frustoconical shape.

6. Syringe (20) according to claim 1, characterized in that the external shape of the end-piece (10) is compatible with a connector of the Luer type.

7. Syringe (20) according to claim 1, characterized in that the said end-piece (10) has a symmetry of revolution relative to its longitudinal axis A.

8. Syringe (20) according to claim 7, characterized in that the external diameter of the proximal end of the end-piece (10) lies within the range from 4.30 to 4.50 mm.

9. Syringe (20) according to claim 7, characterized in that the external diameter of the distal end (14) of the end-piece (10) lies within the range from 3.90 to 4.10 mm.

10. Syringe (20) according to claim 7, characterized in that the average diameter of the second portion (13) of the channel (11) lies within the range from 1.00 to 1.30 mm.

11. Syringe (20) according to claim 7, characterized in that the average diameter of the first portion (12) of the channel (11) lies within the range from 1.60 to 1.90 mm.

12. Syringe (20) according to claim 1, characterized in that the length of the first portion (12) of the channel (11) along the longitudinal axis A of the end-piece (10) lies within the range from 5.60 to 7.00 mm.

13. Syringe (20) according to claim 1, characterized in that the transition zone (16) has a length along the longitudinal axis lying within the range from 0.30 to 2.00 mm.

14. Syringe (20) according to claim 1, characterized in that the said glass is borosilicate glass.

15. Syringe (20) according to claim 1, characterized in that the syringe (20) and the end-piece (10) are made in a single piece of polymer chosen from polycarbonate, polypropylene, the cyclo olefin copolymers (COC), and their blends.

16. Syringe (20) according to claim 15, characterized in that the said polymer is polycarbonate.

17. Syringe (20) according to claim 1, characterized in that the end-piece (10) also comprises a circular groove (18) suitable for assembling a Luer Lock adapter to the said end-piece (10), the said circular groove (18) being situated on the outer surface of the said end-piece (10) between the proximal end (15) of the end-piece (10) and the transition zone (16) of the channel (11).

18. Syringe (20) according to claim 17, characterized in that the said circular groove (18) having a length along the longitudinal axis A of the end-piece (10) defining a proximal edge (18a) and a distal edge (18b) of the said circular groove (18), the distal edge (18b) of the circular groove (18) is situated at a distance of at least 7.50 mm from the free distal end (14) of the end-piece (10).

19. Syringe (20) according to claim 1, characterized in that the end-piece (10) is a Luer Lock end-piece.

20. Syringe (20) according to claim 1, characterized in that the syringe (20) is furnished with a Luer Lock adapter.

21. Syringe (20) according to claim 1, characterized in that the syringe (20) is pre-filled.

* * * * *